United States Patent
Kojima

(10) Patent No.: US 9,339,414 B2
(45) Date of Patent: May 17, 2016

(54) IRRADIATING DEVICE AND PROGRAM

(71) Applicant: CHUKYO MEDICAL CO., INC., Nagoya-shi, Aichi (JP)

(72) Inventor: Takashi Kojima, Nagoya (JP)

(73) Assignee: CHUKYO MEDICAL CO., INC., Nagoya-Shi, Aichi (JP)

( * ) Notice: Subject to any disclaimer, the term of this patent is extended or adjusted under 35 U.S.C. 154(b) by 281 days.

(21) Appl. No.: 14/264,293

(22) Filed: Apr. 29, 2014

(65) Prior Publication Data

US 2015/0305942 A1    Oct. 29, 2015

(51) Int. Cl.
*A61B 18/20*    (2006.01)
*A61F 9/008*    (2006.01)

(52) U.S. Cl.
CPC ... *A61F 9/00834* (2013.01); *A61F 2009/00872* (2013.01)

(58) Field of Classification Search
CPC .............. A61F 2009/00872; A61F 9/008
See application file for complete search history.

(56) References Cited

U.S. PATENT DOCUMENTS

| | | | |
|---|---|---|---|
| 2005/0143717 A1* | 6/2005 | Peyman ............... | A61F 9/008 606/5 |
| 2008/0082086 A1 | 4/2008 | Kurtz et al. | |
| 2010/0004641 A1* | 1/2010 | Frey .................... | A61F 9/008 606/4 |
| 2011/0172649 A1* | 7/2011 | Schuele ................ | A61F 9/008 606/4 |
| 2014/0081249 A1* | 3/2014 | Bischoff ............. | A61F 9/00827 606/5 |

FOREIGN PATENT DOCUMENTS

| | | | |
|---|---|---|---|
| JP | H0938129 | A | 2/1997 |
| JP | 2005312921 | A | 11/2005 |
| JP | 2011507559 | A | 3/2010 |
| JP | 2010520801 | A | 6/2010 |
| JP | 2012091053 | A | 5/2012 |
| WO | 2011011202 | A1 | 1/2011 |
| WO | 2012076033 | A1 | 6/2012 |

* cited by examiner

*Primary Examiner* — Ahmed Farah
*Assistant Examiner* — Jeffrey Lipitz
(74) *Attorney, Agent, or Firm* — Bacon & Thomas, PLLC

(57) ABSTRACT

The invention provides an irradiating device and a program which can appropriately set a cross sectional shape of human tissue at a time of incising the human tissue by beam irradiation. For example, when a cornea (100) is incised by an irradiating device which outputs femtosecond laser, a cross sectional shape in an intersecting direction to a direction of advancing to a back surface side from a front surface side of the cornea in an incision (101) is set to a non-rectilinear shape, for example, a circular arc shape. As a result, there can be achieved effects such as suppression of drawing of the incision in the case of inserting the instrument by opening the incision, and self-closing of the incised site.

4 Claims, 8 Drawing Sheets

A-A CROSS SECTION

A-A CROSS SECTION

A-A CROSS SECTION

B-B CROSS SECTION

C-C CROSS SECTION

D-D CROSS SECTION

B-B CROSS SECTION

C-C CROSS SECTION

D-D CROSS SECTION

B-B CROSS SECTION

C-C CROSS SECTION

D-D CROSS SECTION

A-A CROSS SECTION

A-A CROSS SECTION

IRRADIATING DEVICE AND PROGRAM

BACKGROUND OF THE INVENTION

1. Field of the Invention

The present invention relates to an irradiating device and a program.

2. Description of the Conventional Art

There is a method which uses an optical beam such as laser at a time of performing an operation. As an example thereof, there can be listed up a method which uses femtosecond laser having a pulse width (a pulse cycle) between about 100 femtosecond and 10 picosecond in an eye surgery. The technique has targeted at lasik in the initial stages, however, broadens its target to a cataract operation in recent years. In the following patent document 1, there is disclosed a technique which aims at accurately seating an intraocular lens in a capsule by applying an asymmetric feature portion to an incised portion or an intraocular lens in the case of making an incision on the lens capsule of a patient while using the femtosecond laser.

PRIOR ART DOCUMENT

Patent Document

Patent Document 1: Japanese Unexamined Patent Publication No. 2012-91053

SUMMARY OF THE INVENTION

Problem to be Solved by the Invention

There is a case that any attention is not particularly paid to a cross sectional shape of an incised site when incising human tissue. For example, when incising cornea in the prior art, any attention seems to be not particularly paid to the cross sectional shape of the incised site (here, the cross section is a cross section in a direction of intersecting a forward direction of the incision from a front surface of the cornea to a back surface, and same applied to the below as long as any different description is not given). Even in the case that the cornea is incised by the laser such as the patent document 1, the cross sectional shape of the incised site is not particularly considered, but is considered to be a simple linear shape, for example.

However, according to the knowledge obtained by the inventor of the present invention, if the cross sectional shape of the incised site is not limited to the linear shape in the incision of the cornea, but is set to a more appropriate shape, an effect which can not be obtained conventionally can be achieved. For example, in the case of employing an incised site having a cross sectional shape formed into a circular arc shape of an inverted-V shape, a convex side among both sides of the incision collapses onto an intraocular side when inserting the intraocular lens into the intraocular side after the incision. Accordingly, there can be achieved effects that drawing of the incised site is suppressed, or self-closing of the incised site is facilitated.

Accordingly, taking the above matters into consideration, an object of the present invention is to provide an irradiating device and a program which can appropriately set a cross sectional shape of human tissue at a time of incising the human tissue by beam irradiation.

Means for Solving the Problem

In order to achieve the object mentioned above, an irradiating device according to the present invention is provided with an output means which outputs operation beam having a function of making an incision on a cornea of an eye, a control means which controls at least an irradiating direction of the operation beam in such a manner as to form an incised site for inserting an intraocular lens into an interior of the eye, the incised site penetrating from an outer front surface of the cornea of the eye to an inner front surface, by the operation beam output from the output means, and a setting means which sets a cross sectional shape in a direction intersecting an advancing direction from an opening of the outer front surface of the cornea in the incised site toward an opening of the inner front surface, to the other linear shape than a rectilinear shape in which a convex shape collapsing onto the inner front surface from the outer front surface of the cornea is formed at least in one of both sides of the incised site, in the case of inserting the intraocular lens through the incised site, and accepts an input from a user, wherein the setting means is provided with a display means which displays an image of an operation part, and a superposition setting means which superposes the image of the operation part displayed by the display means, and accepts an input setting a shape of an advancing route heading for the inner front surface from the outer front surface of the cornea of the eye in the incised site, and a cross sectional shape in a direction intersecting the advancing route in the incised site, and the superposition setting means can accept a cross sectional shape in which the cross sectional shape changes in correspondence to the position on the advancing route in the incised site.

Further, the film-like tissue may be constituted by a film-like tissue in the eye. As a result, in the incision of the film-like tissue of the eye, there can be achieved effects such as suppression of drawing of the incision in the case of inserting the instrument by opening the incision, and self-closing of the incised site.

Further, the film-like tissue may be constituted by a cornea of the eye. As a result, in the incision of the cornea of the eye, there can be achieved the effects such as the suppression of the drawing of the incision in the case of inserting the instrument by opening the incision, and facilitation of the self-closing of the incised site.

Further, the other linear shape than the rectilinear shape may be constituted by a shape in which a convex shape collapsing from one side of the first front surface and the second front surface onto the other side is formed at least in one of both sides of the incised site, in the case of inserting an object through the incised site. As a result, there can be achieved the effects such as the suppression of the drawing of the incision in the case of inserting the instrument by opening the incision, and the facilitation of the self-closing of the incised site, on the basis of the formation of the convex shape.

Further, the setting means may set the cross sectional shape in the incised site in correspondence to a position between the first front surface and the second front surface in the incised site. As a result, there can be achieved the effects such as the suppression of the drawing of the incision in the case of inserting the instrument by opening the incision, and the facilitation of the self-closing of the incised site, by appropriately setting the cross sectional shape in correspondence to the position within the incision.

Further, the operation beam may be constituted by femtosecond laser. As a result, there can be achieved the effects such as the suppression of the drawing of the incision in the case of inserting the instrument by opening the incision, and the facilitation of the self-closing of the incised site, in the incision using the femtosecond laser.

Further, a program according to the present invention makes a computer function as an output means which instructs an output of operation beam having a function of making an incision on human tissue, a control means which controls at least an irradiating direction of the operation beam in such a manner as to form an incised site heading for a second front surface from a first front surface of a film-like tissue, in relation to the film-like tissue of human body by an the operation beam output on the basis of the instruction of the output means, and a setting means which sets a cross sectional shape in a direction intersecting a direction heading for the second front surface from the first front surface in the incised site to the other linear shape than a rectilinear shape. As a result, there can be achieved the effects such as the suppression of the drawing of the incision in the case of inserting the instrument by opening the incision, and the facilitation of the self-closing of the incised site, by setting the cross sectional shape to the other linear shape than the rectilinear shape.

Figure 1:
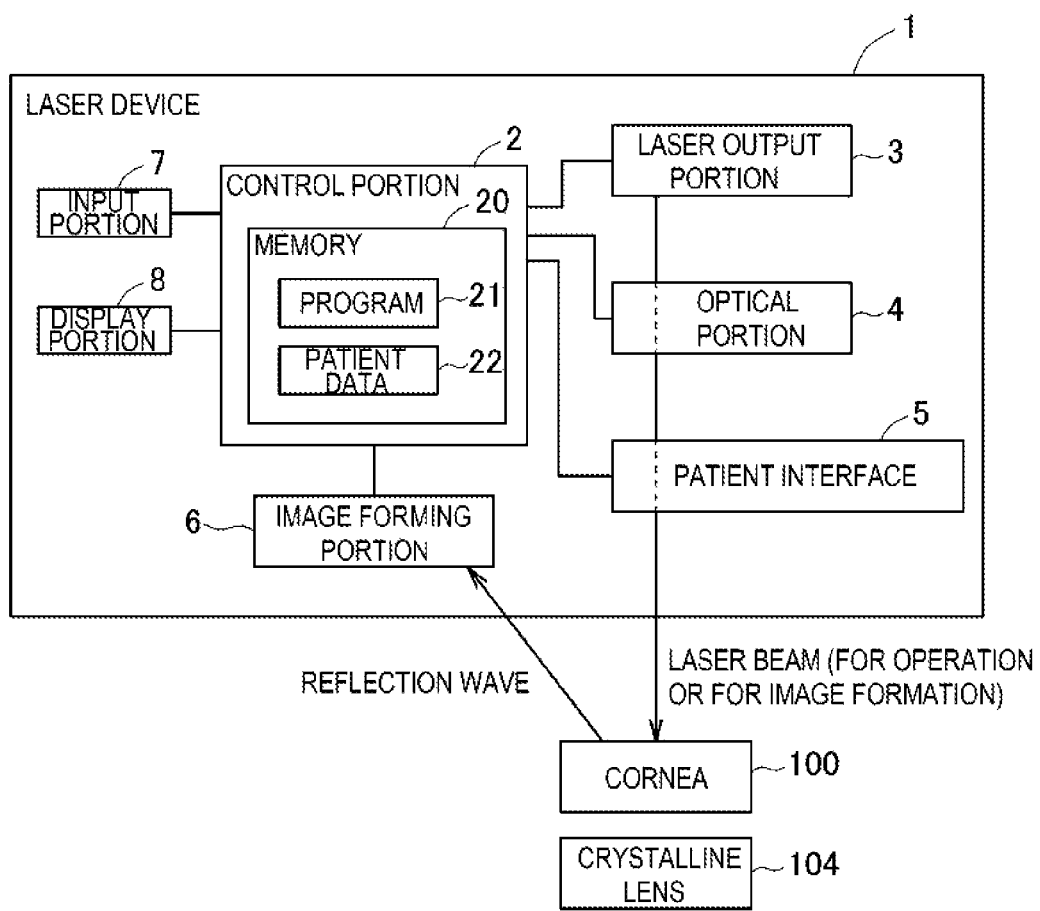
FIG. 1 is a view showing an example of an internal structure in an embodiment of an irradiating device according to the present invention.

DESCRIPTION OF REFERENCE NUMERALS 1 laser device (irradiating device)
2 control portion
3 laser output portion
21 program

DETAILED DESCRIPTION OF PREFERRED EMBODIMENT

A description will be given below of an embodiment of the present invention with reference to the accompanying draw-ings. FIG. 1 is a view conceptually showing an internal structure of a laser device 1 which is an example of an irradiating devices of the present invention. The laser device 1 is provided with a control portion 2, a laser output portion 3, an optical portion 4, a patient interface 5, an image forming portion 6, an input portion 7 and a display portion 8.

The control portion 2 is a section which executes the control of the laser device 1. The control portion 2 has the same structure as that of a normal computer, and is provided with CPU which carries out various instructions and computations relating to the present invention, RAM which is a volatile memory portion and serves as a work area of the CPU, and a nonvolatile memory portion 20 (a memory) which stores data and programs necessary in various information processing in the CPU. The memory 20 stores a program 21 which describes a control procedure of the present invention, and various data 22 of a patient treated by the laser device 1 (details will be mentioned later).

The laser output portion 3 is a section which outputs laser for the purpose of incision, for example, of the human tissue. The laser output by the laser output portion 3 may be constituted, for example, by femtosecond laser. The femtosecond laser is the pulse-like laser as is well known, and is the laser in which its pulse width (or a pulse cycle in a cyclic case) is in a range, for example, between 100 femtosecond and 10 picosecond. The pulse width and the cycle of the output laser are controlled by the control portion 2.

The optical portion 4 is constructed by an optical system, that is, a lens, a reflecting mirror and a prism, and is a section which directs the laser output from the laser output portion 3 to a subject to be irradiated, on the basis of an action such as refraction, reflection, concentration or divergence of the laser beam. The control portion 2 irradiates the laser output from the laser output portion 3 to a desired position of the subject to be irradiated, by controlling the optical portion 4.

The patient interface 5 is a section which comes into contact with the patient in the laser device 1. In the case that the patient interface 5 comes into contact with the patient, a positional relationship between the laser device 1 and the patient is fixed, and the laser is stably irradiated onto a desired position.

Figure 18:
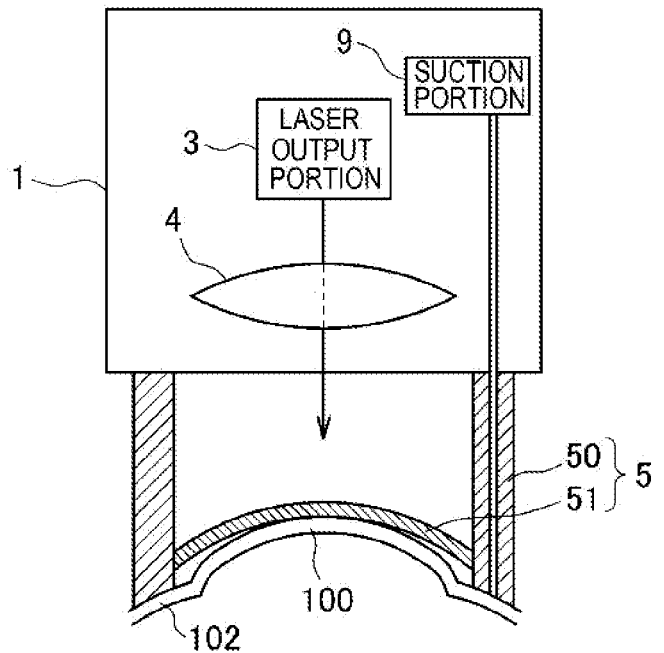
FIG. 18 is a view showing an example of a structure of a patient interface.

FIG. 18 shows an embodiment of the patient interface 5. In the example of FIG. 18, the subject to be irradiated by the laser is set to an eye of the human body (a cornea 100 or a crystalline lens of the eye). In the structure example of FIG. 18, the patient interface 5 is provided with a tube portion 50 which has a tubular shape, and a contact glass 51 which comes into contact with the corner 100 of the patient. The tube portion 50 is fixed to the eye of the patient by bringing the tube portion 50 into contact with the eye of the patient in such a manner that the tubular shape surrounds an operation site, and sucking the air in the contact portion by the suction portion 9 at the using time.

At this time, by making the contact glass 51 come into contact with the cornea 100, a positional relationship of the patient interface 5 and further the laser device 1 with the eye of the patient can be stably fixed, in cooperation with the contact of the contact glass 51 with the cornea 51. The contact glass 51 is made, for example, of a glass so as to penetrate the laser beam. The contact glass 51 may be constituted by a flat applanation glass, and may be curved so as to have a lens function.

Returning to FIG. 1, the image forming portion 6 acquires a reflection wave which is formed by reflection of the laser beam output from the laser output portion 3 on the subject to be irradiated (for example, the corner 100 or the crystalline lens 104), and forms a three-dimensional image of the operation part and the periphery of the operation part, from information of a reflection wave, for example, delay time of the reflection wave.

The input portion 7 is constituted by various buttons or a ten-key numeric keypad, and is a section which accepts the input from the user relating to the present invention. Any specific aspect of the input portion 7 is not limited. Input content to the input portion 7 is sent to the control portion 2. The display portion 8 is constituted, for example, by a liquid crystal display, and displays the information relating to the present invention toward the user, on the basis of the control of the control portion 2.

On the basis of the structure mentioned above, the laser device 1 irradiates the laser beam, for example, for the incision of the human tissue. The laser beam is output from the laser output portion 3 on the basis of the instruction from the control portion 2, and the output laser beam is irradiated to the human tissue through the patient interface 5 under the action of the refraction and the reflection in the optical portion 4 on the basis of the control of the control portion 2.

Figure 19:
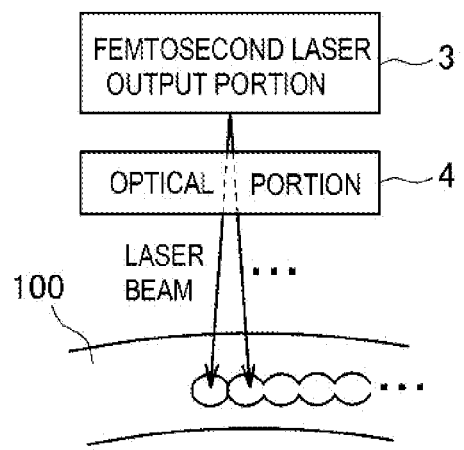
FIG. 19 is a view showing an example of an incision state by femtosecond laser.

FIG. 19 is a view schematically showing a principle of the incision of the human tissue, for example, the corner 100 by the laser beam which is irradiated by the laser device 1. In FIG. 19, there is shown an example in the case that the laser beam output from the laser device 1 constituted by the femtosecond laser. As is well known, the femtosecond laser device creates plasma explosion within the subject to be irradiated and forms a cavity by irradiating pulse-like laser beam having a pulse width (a pulse cycle) between about 100 femtosecond and 10 picosecond. Since the cavities are continuously formed so as to be spaced within the subject to be irradiated and are connected, a cutting plane such as a perforated line is formed. At this time, a depth of the cutting plane can be set, and a shallower portion than the cutting plane is not injured.

Purposes of the laser irradiation of the laser device 1 are mainly constituted by the operation (the incision) and the image formation. In the case that the incision is aimed, the irradiated portion is incised by irradiating the laser beam to the incision section of the human tissue. In the case that the image formation is aimed, the reflection wave of the laser beam irradiated to the operation part and the periphery of the operation part is received by the image forming portion 6. The image forming portion 6 forms the three-dimensional image of the operation part and the periphery of the operation part on the basis of the information of the reflection wave, for example, the delay time of the reflection wave, as mentioned above. The control portion 2 controls (adjusts) a direction or a depth of the surgical laser on the basis of the three-dimensional image. The principle of the image formation by the image forming portion 6 may be set, for example, to a known optical coherence tomography (OCT).

The following description will show the case that the laser irradiation by the laser device 1 is the irradiation on the cornea or the crystalline lens in the cataract operation of the eye. Generally, at the cataract operating time, there are carried out treatments such as an incision of the cornea, an incision of the crystalline lens anterior capsule, an emulsification suction treatment within the crystalline lens by the ultrasonic wave, an insertion into an intraocular of the intraocular lens and an arrangement within the lens capsule, however, the incision of the cornea, the incision of the crystalline lens anterior capsule and a fragmentation of a nucleus lentis among them may be carried out in the laser device 1.

Figure 2:
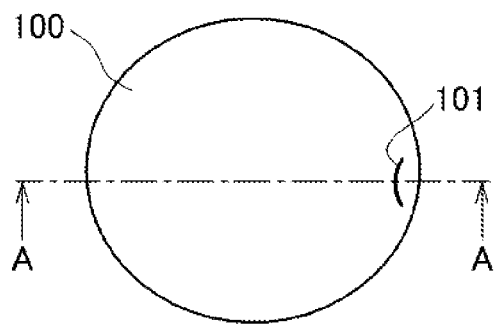
FIG. 2 is a view showing an example of a cornea incision.
Figure 3:
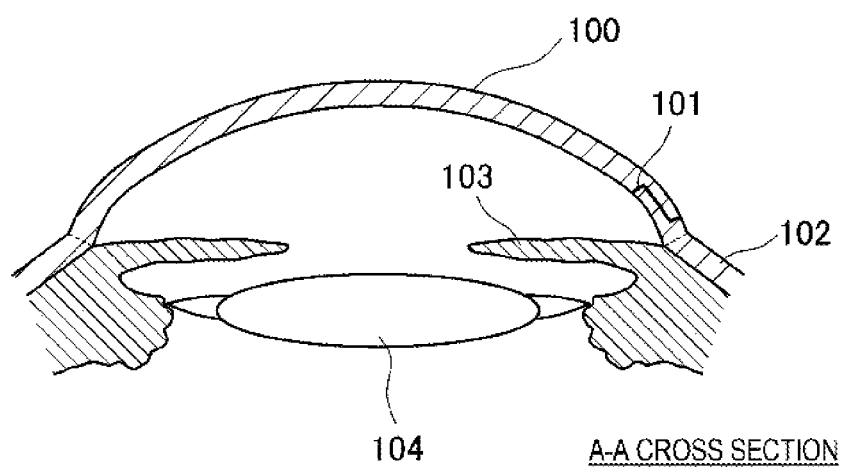
FIG. 3 is a cross sectional view along a line A-A in a first example of an incision shape.
Figure 4:
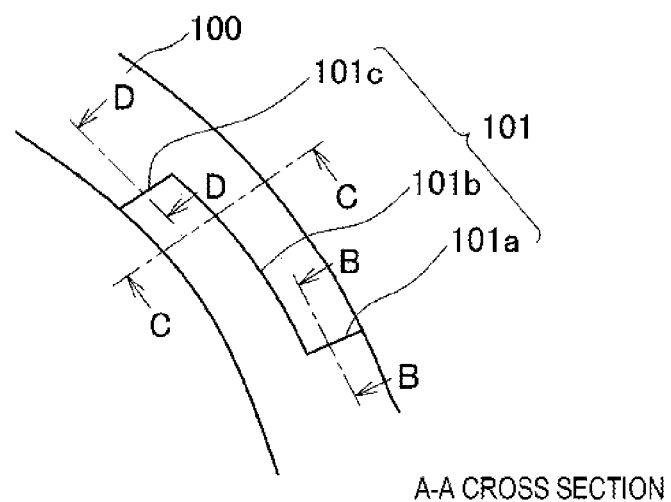
FIG. 4 is an enlarged view of FIG. 3.

FIGS. 2 to 7 show an example of the cornea incision shape by the laser device 1. FIG. 2 shows the example of the cornea 100 as seen from a visual axis direction and the incision 101 (the incised site) formed in the cornea 100. FIG. 3 is a cross sectional view along a line A-A in FIG. 2, and FIG. 4 is an enlarged view of FIG. 3. FIGS. 3 and 4 show an example of a cross sectional shape from a front surface (a surface in an outer side of the human body) side of the cornea 100 in the incision 101 toward a back surface (a surface in an inner side of the human body). In the cataract operation, a plurality of incisions are carried out. The plurality of incisions include an incision (a main incision) for inserting the intraocular lens and an ultrasonic wave chip, and an incision for inserting a hook. However, the illustrated incision may be constituted by any incision among them.

In the example from FIG. 2 to FIG. 7, the incision 101 is formed at a position in a side edge portion which is closer to the sclera 102 in the cornea 100. As shown in FIG. 2, a shape of the incision 101 as seen from the front surface is a curved shape. More specifically, the shape is a bent shape which is concave toward a visual axis of the eye (a central axis of the eye). Further, as shown in FIGS. 3 and 4, a cross sectional shape of the incision 101 by a cross section including the visual axis is a flection shape or a zigzag shape. More specifically, the incision 101 is constituted by a portion 101a which first of all advances from the front surface of the cornea to an internal direction of the eye, a portion 101b which is bent from the portion 101a and advances approximately in parallel to the cornea front surface, and a portion 101c which is again bent from the portion 101b and reaches the cornea back surface side.

The position where the portion 101b is formed may be set optionally, for example, to a position having a depth which is about half of a thickness of the cornea 101. Further, the cross sectional shapes shown in FIG. 4 of the portions 101a, 101b and 101c may be formed into a rectilinear shape or a curved shape. A section between the portions 101a and 101b and a section between the portions 101b and 101c may be bent at an acute angle (a right angle or an obtuse angle), or may be smoothly bent like a curve.

Figure 5:
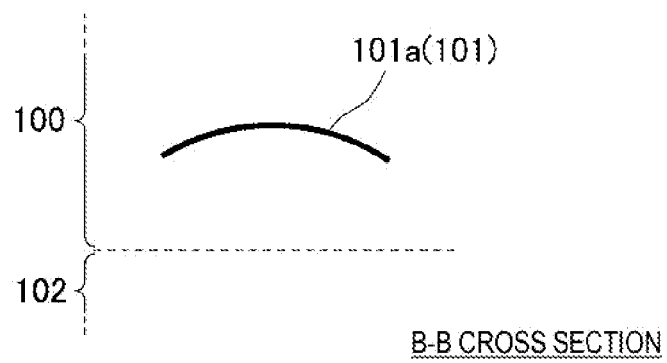
FIG. 5 is a cross sectional view along a line B-B in the first example of the incision shape.
Figure 6:
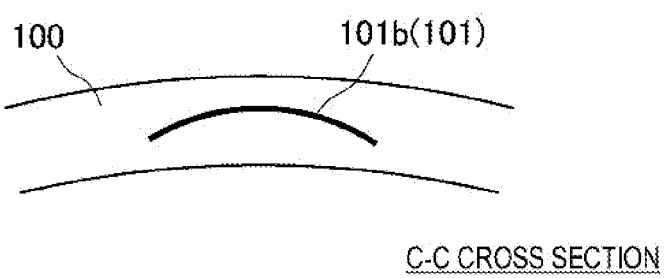
FIG. 6 is a cross sectional view along a line C-C in the first example of the incision shape.
Figure 7:
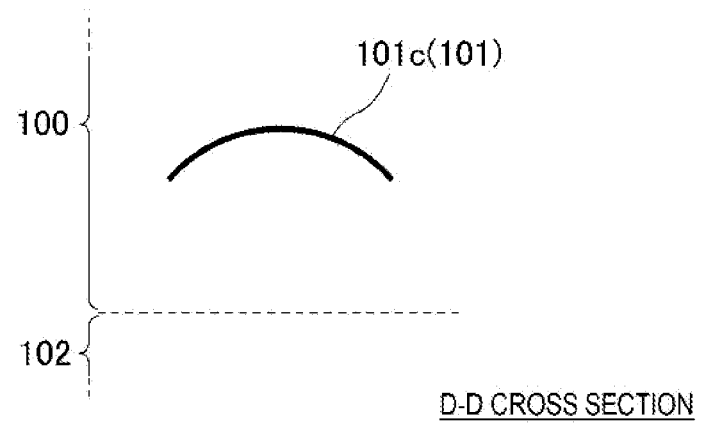
FIG. 7 is a cross sectional view along a line D-D in the first example of the incision shape.

FIGS. 5 to 7 respectively show examples of a cross section along a line B-B, a cross section along a line C-C and a cross section along a line D-D of the incision 101 in FIG. 4. In the example of FIG. 5, the cross sectional shape of the portion 101a is a curved shape (a circular arc shape) which is convex toward the visual axis side of the eye. In the example of FIG. 6, the cross sectional shape is a curved shape which is convex toward the front surface side of the cornea 100 continuously from the shape of FIG. 5. In the example of FIG. 7, the cross sectional shape is a curved shape which is convex toward the visual axis side of the eye continuously from the shape of FIG. 6. In the incision 101, the cross sectional shapes as shown in FIGS. 5 to 7 are deemed to be continuously formed from the front surface side of the cornea 100 toward the back surface side.

In the case of the conventional incision, the cross sectional shapes shown in FIGS. 5 to 7 have been constituted by the rectilinear shape. In this case, when the incision is opened, for example, for inserting the intraocular lens or the ultrasonic wave chip into the eye, there has been a case that a side end of the incision ruptures and a trouble of elongation of the incision is caused.

On the contrary, in the case of the cross sectional shapes shown in FIGS. 5 to 7, one portion (a lower portion in FIGS. 5 to 7) among both side portions of the incision 101 can be collapsed onto the direction of the intraocular when opening the incision 101. As a result, the intraocular lens and the ultrasonic wave chip can be inserted without trouble from a gap which is formed by the collapse. Therefore, it is possible to effectively suppress the conventional drawing of the incision. Further, in the case of the cross sectional shapes in FIGS. 5 to 7, an effect of self-closing of the incision is considered to be improved.

Figure 8:
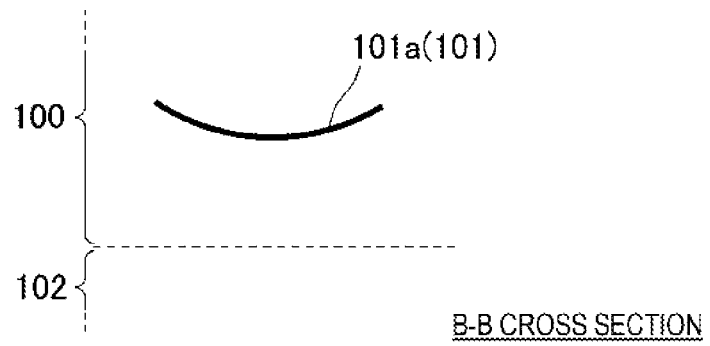
FIG. 8 is a cross sectional view along a line B-B in a second example of the incision shape.
Figure 9:
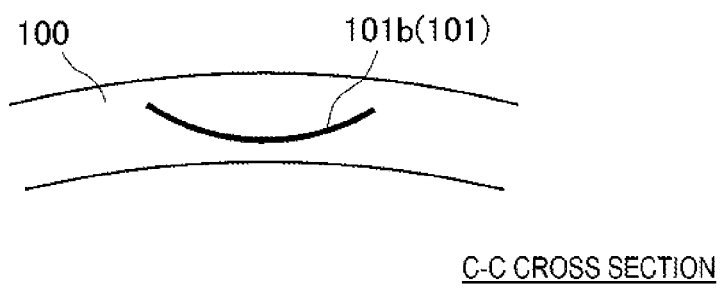
FIG. 9 is a cross sectional view along a line C-C in the second example of the incision shape.
Figure 10:
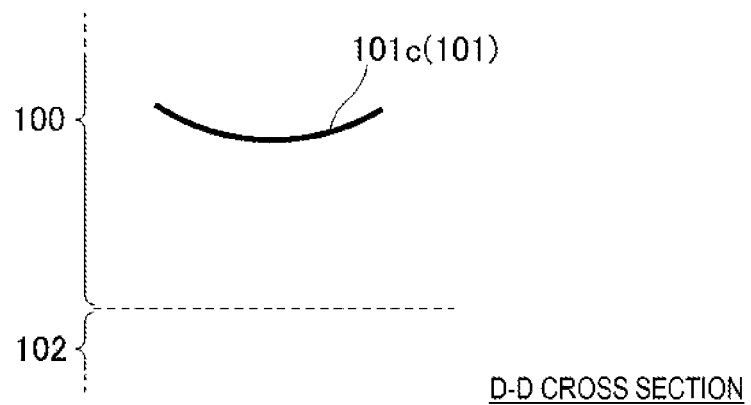
FIG. 10 is a cross sectional view along a line D-D in the second example of the incision shape.

The cross sectional shape of the incision in the present invention is not limited to the examples in FIGS. 5 to 7. A second example of the cross sectional shape is shown in FIGS. 8 to 10. In the example of FIG. 8, the cross sectional shape of the portion 101a is formed into a curved shape (a circular arc shape) which is concave toward the visual axis side of the eye. In the example of FIG. 9, the cross sectional shape is formed into a curved shape which is concave toward the front surface side of the cornea 100 continuously from the shape of FIG. 8. In the example of FIG. 10, the cross sectional shape is formed into a curved shape which is concave toward the visual axis side of the eye continuously from the shape of FIG. 9.

In the incision 101, the cross sectional shapes shown from FIG. 8 to FIG. 10 are deemed to be continuously formed from the front surface side of the cornea 100 toward the back surface side. The cross sectional shapes in FIGS. 8 to 10 are considered not to be easy even by deforming a scalpel shape in the case of the incision by the scalpel. As a result, the present invention can realize the cross sectional shape which has not been conventionally realized.

Figure 11:
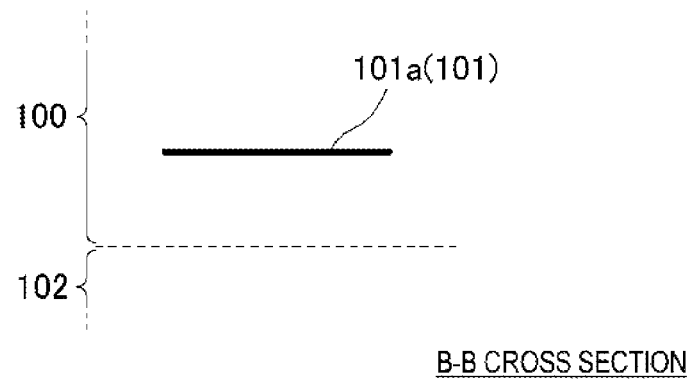
FIG. 11 is a cross sectional view along a line B-B in a third example of the incision shape.
Figure 12:
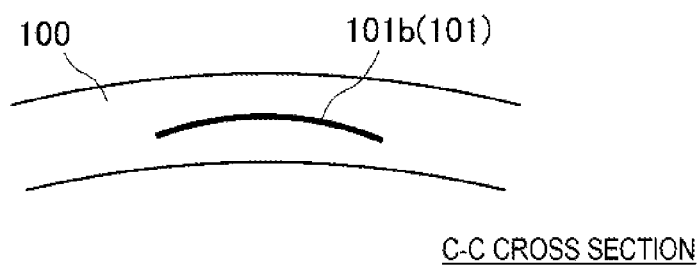
FIG. 12 is a cross sectional view along a line C-C in the third example of the incision shape.
Figure 13:
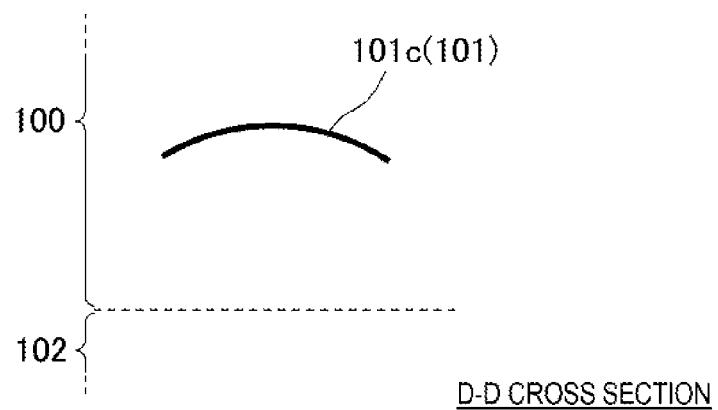
FIG. 13 is a cross sectional view along a line D-D in the third example of the incision shape.

A third example of the cross sectional shape is shown in FIGS. 11 to 13. In the example, specifically, a cross section of a portion 101a in FIG. 11 is formed into a circular arc shape, a cross sectional shape of a portion 101b in FIG. 12 is formed into a rectilinear shape, and a cross sectional shape of a portion 101c in FIG. 13 is formed into a circular arc shape which has an inversed code of curvature to that of the portion 101a in FIG. 11. In the example from FIG. 11 to FIG. 13, the curvature may be set to be changed continuously (simply) according to the advance of the incision 101 from the front surface side of the cornea 100 to the back surface side.

Alternatively, in the case that the curvature of FIG. 11 is set to a positive curvature inversely to FIGS. 11 to 13, the curvature may be changed so that the portion 101a is a circular arc having a negative curvature, the portion 101b is a straight line, and the portion 101c is a circular arc having a positive curvature. Further, generally, the curvature may be set to be increased or decreased continuously (simply) according to the advance of the incision 101 from the front surface side of the cornea 100 to the back surface side. Further, the curvature may be set to be changed (increased or decreased) according to an advancing degree of the incision from the front surface side of the cornea to the back surface side, without being limited to the simple increase or the simple decrease. Without being limited to the examples, according to the present invention, the cross sectional shape of the incision may be set according to an advancing degree of the incision from the front surface side of the cornea to the back surface side. In the case that the cross sectional shape is determined according to the degree of the advance of the incision from the front surface side of the cornea 100 to the back surface side as mentioned above, the present invention can realize the cross sectional shape which has not been conventionally realized, since the incision by the scalpel is considered not to be easy even by deforming the scalpel shape.

Figure 14:
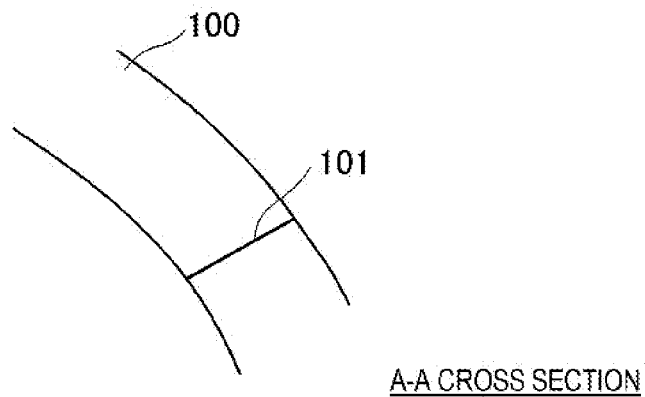
FIG. 14 is a view showing a second example of the cross section along the line A-A.
Figure 15:
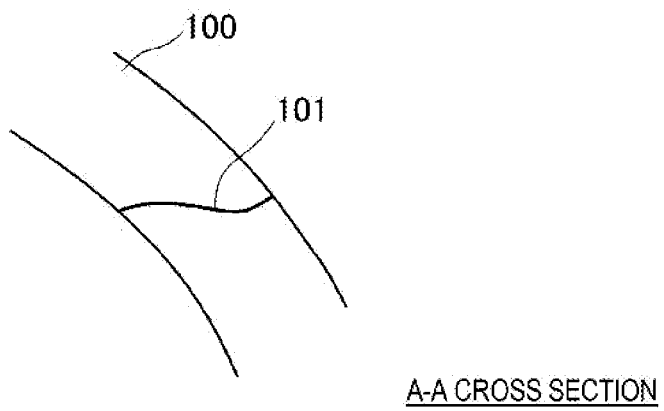
FIG. 15 is a view showing a third example of the cross section along the line A-A.

Further, the cross sectional shape including the visual axis in the incision is not limited to the examples in FIGS. 3 and 4. A second example of the cross section along the line A-A is shown in FIG. 14. In this example, the incision is advanced from the front surface side of the cornea 100 to the back surface side (approximately) rectilinearly in its cross section. A third example of the cross section along the line A-A is shown in FIG. 15. In this example, the incision is advanced from the front surface side of the cornea 100 to the back surface side like an S-shaped form in its cross section. The cross sectional shape by the cross section including the visual axis of the incision is not limited without being limited to the examples of FIGS. 4, 14 and 15.

Figure 16:
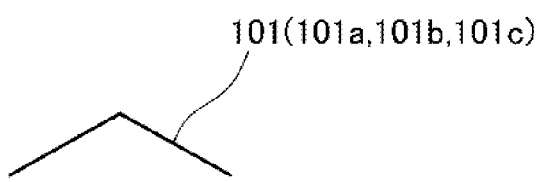
FIG. 16 is a view showing a fourth example of the incision shape.
Figure 17:
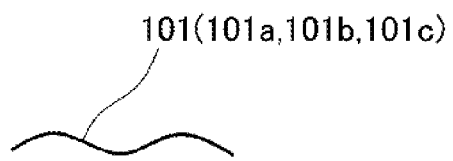
FIG. 17 is a view showing a fifth example of the incision shape.

The present invention is not limited to the cross sectional shapes shown in FIGS. 5 to 13, but can employ cross sectional shapes, for example, shown in FIGS. 16 and 17. In the example of FIG. 16, the cross sectional shape of the incision 101 is formed into a V-shaped form (or an inverted V-shaped form). In the example of FIG. 17, the cross sectional shape of the incision 101 is formed into a wavy shape. In the case of FIGS. 16 and 17, any of an upper side and a lower side of the drawing can be set to the sclera side.

Whichever cross sectional shape of the incision, such a convex shape as to collapse onto the back surface side from the front surface side of the cornea is formed in at least one of both sides of the incised site, in the case that any subject is inserted into the eye from the outside of the eye through the incised site. (For example, in the case of FIGS. 5 to 7, the lower side of the drawing among both the upper and lower sides in the drawing of the incision 101 is formed into the convex shape. The upper side of the drawing of the incision 101 is formed into the convex shape in FIGS. 8 to 10.) According to the cross sectional shapes mentioned above, there can be considered the suppression of the drawing of the incision at the inserting time of the subject, and the improvement of the self-closing capacity of the incision.

An example of the treatment procedure of the laser device 1 for making an incision as mentioned above is shown in FIG. 20. The treatment procedure of FIG. 20 is previously programmed and is stored as the program in the memory 20, and may be automatically executed except the treatment which the control portion 2 calls and the user manually carried out.

Figure 20:
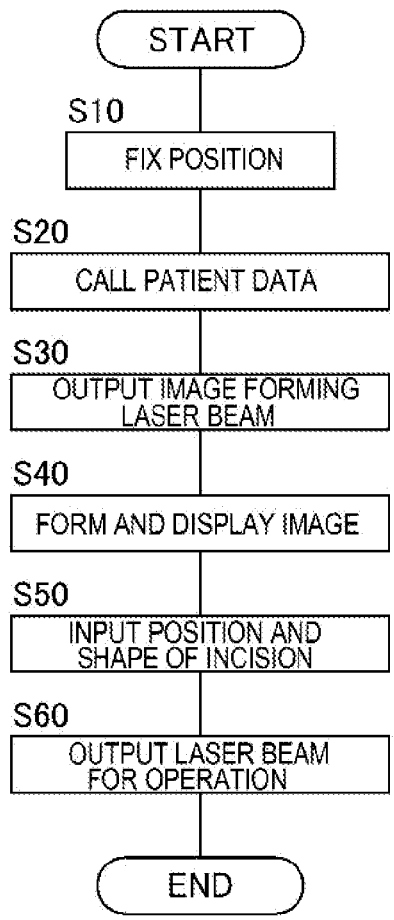
FIG. 20 is a flow chart showing an example of a treatment procedure in an irradiating device according to the present invention.

In the treatment procedure of FIG. 20, S10 first of all fixes a relative positional relationship between the laser device 1 and the operation part of the patient. More specifically, the laser device 1 may be fixed to the eye of the patient by the patient interface 5, for example, as shown in FIG. 18 as mentioned above.

Next, the control portion 2 calls the patient data 22 from the memory 2 in S20. The patient data 22 may be constituted by various data of the patient which is the subject to be operated by the laser device 1, for example, data of the past operated position, and may be stored the past medical opportunity. S20 may display on the display portion 8 the patient data which is further called. The user may make reference to the information, for example, in an input in S50 mentioned later. The patient data 22 and the procedure in S20 may be omitted.

Next, the control portion 2 instructs in S30 an output of an image forming laser to the laser output portion 3. In response to the instruction, the laser output portion 3 irradiates the output of the image forming laser toward the operation part and its periphery. Further, the image forming portion 6 receives in S40 the reflected laser wave which is reflected by the operation part, and accordingly forms an image (for example, a three-dimensional image) of the operation part and its periphery. The control portion 2 may acquire the image and display by the display portion 8.

Next, the user inputs in S50 the position and the shape of the incision by using the input portion 7. More specifically, for example, the user first of all inputs a cross sectional shape relating to the cross section including the visual axis of the incision (for example, the shape shown in the cross sections along the lines A-A of FIGS. 4, 14 and 15 in the examples), next designates a desired point on the cross sectional shape, and inputs a cross sectional shape of the incision at the position of the point (the cross section is here a section in an intersecting direction in which the incision advances from the front surface of the cornea to the back surface).

Some aspects can be employed as the inputting method using the input portion 7. For example, a position of each of points of the incision surface may be numerically input. For example, in the case that the cross sectional shape of the incision is set to the circular arc shape as shown in FIGS. 6 to 10, the curvature of the circular arc may be numerically input. Alternatively, the display portion 8 may be constituted by a touch panel, and the position of each of the points of the incision surface may be designated by a pen on the image of the operation part displayed on the display portion 8.

Alternatively, some of representative incision shapes may be previously described within the program 21 and the user may select a desired shape among them. Further, the user may display in a superposing manner the desired shape on the image of the operation part and may finely correct the desired shape by a pen or a numerical input. In order to confirm by the image whether or not the input content by the user is appropriate whichever input aspect, the incision shape set by the user input may be superposed on the image of the operation part and its periphery (the image formed by S40) so as to be displayed on the display portion 8.

Next, the control portion 2 instructs in S60 the laser output portion 3 to output the surgical laser so as to form the incision having the shape set in S50. As a result, the incision is formed within the cornea of the patient according to a principle shown in FIG. 19. The above is the treatment procedure of FIG. 20.

The treatment procedure of FIG. 20 is only an example, and may be appropriately changed. For example, the treatment of S50 may be constituted by an aspect which is carried out prior to the treatment of FIG. 20. In this case, more specifically, the data of the shape of the patient cornea may be acquired (by executing S30 and S4), for example, in the past medical examination, and the treatment of S50 may be executed on the data. Further, the shape data of the patient cornea and the data of the incision shape may be stored in the memory 2 while being included in the patient data 22, and may be called by S20.

The treatment procedure of FIG. 20 is embedded as a part of all the cataract operation. An example of the other procedure than the procedure of the treatment of FIG. 20 is as follows. Prior to (or in succession to) the treatment of FIG. 20, the incision of the crystalline lens anterior capsule is carried out by using the laser device 1. In the incision, for example, a circular incision 105 around the visual axis may be formed in the crystalline lens anterior capsule.

In succession to this, the nucleus of the crystalline lens 104 which is clouded by the cataract is fragmentized by the laser beam of the laser device 1. Further, the nucleus of the crystalline lens 104 which is fragmentized is sucked by using a predetermined ultrasonic emulsifying and sucking device (not shown). At this time, the suction treatment is carried out, for example, by inserting the ultrasonic wave chip of the device into the eye from the incision 101 and further inserting into the crystalline lens through the incision 105. In this case, most nucleus may be fragmentized by the laser device 1, and the remaining part may be fragmentized and sucked by the ultrasonic emulsifying and sucking device.

Figure 21:
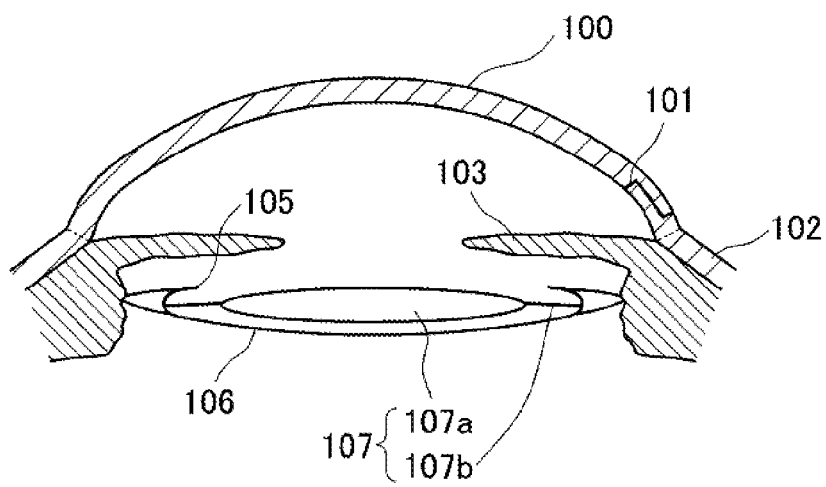
FIG. 21 is a view showing an example of a state in which an intraocular lens is installed.

Subsequently, the intraocular lens 107 is inserted in a state in which the crystalline lens 104 comes to a cavity and the posterior capsule 106 is left. An example of the state is shown in FIG. 21. In this example, the intraocular lens 107 is provided with a lens 107a and a haptic 107b. The haptic 10b is formed into a tactile shape (a haptic shape or a loop shape) from side edges, for example, two positions of the lens 107a, and has an appropriate elasticity. The lens 107a is deemed to have an elasticity.

When installing the intraocular lens, the intraocular lens 107, for example, rounded so as to be formed like a rod is accommodated within an instrument (not shown) such as a predetermined cartridge. Further, a leading end of the instrument is inserted into the eye, for example, from the incision 101, and is further inserted into the posterior capsule 106 beyond the iris 103, and the intraocular lens 107 is delivered from the leading end of the instrument under the state. As a result, the intraocular lens 107 is inserted into the posterior capsule 106, and the haptic 107b normally presses the inner portion of the posterior capsule 106 on the basis of an elastic restoring force. As mentioned above, the intraocular lens 107 is stably positioned and fixed within the posterior capsule 106. The above is an example of the operation procedure in the cataract operation.

The embodiment mentioned above may be modified and changed on the basis of the scope described in claims. For example, the irradiating device is exemplified by the laser device in the embodiment mentioned above, however, the present invention is not limited to this, but can be constituted by a device outputting (optical) beam having a capacity of incising the human tissue. Further, the example of the cornea incision in the cataract is mentioned above, however, the present invention is not limited to this, but can be applied to the incision of the other film-like tissue, for example, the sclera, or can be applied to the other operations than the cataract. Further, the present invention is not limited to the eye, but can be applied to the incision of the human tissue, or the incision, for example, of the film-like portion of the human tissue.

What is claimed is:
1. An irradiating device comprising:
an output means which outputs operation beam having a function of making an incision on a cornea of an eye;
a control means which controls at least an irradiating direction of said operation beam in such a manner as to form an incised site for inserting an intraocular lens into an interior of the eye, the incised site penetrating from an outer front surface of the cornea of the eye to an inner front surface, by the operation beam output from the output means; and
a setting means which sets a cross sectional shape in a direction intersecting an advancing direction from an opening of the outer front surface of the cornea in said incised site toward an opening of the inner front surface, to the other linear shape than a rectilinear shape in which a convex shape collapsing onto the inner front surface from the outer front surface of the cornea is formed at least in one of both sides of said incised site, in the case of inserting the intraocular lens through said incised site, and accepts an input from a user,
wherein said setting means comprises:
a display means which displays an image of an operation part; and
a superposition setting means which superposes the image of the operation part displayed by the display means, and accepts an input setting a shape of an advancing route heading for the inner front surface from the outer front surface of the cornea of the eye in the incised site, and a cross sectional shape in a direction intersecting said advancing route in the incised site, and
wherein said superposition setting means can accept a cross sectional shape in which said cross sectional shape changes in correspondence to the position on said advancing route in the incised site.

2. The irradiating device according to claim 1, wherein said setting means comprises a second setting means which can accept both of an input from a user for setting said linear shape to a linear shape which is convex toward a center of the cornea or a front surface outside the cornea, and an input from the user for setting said linear shape to a linear shape which is concave toward the center of the cornea or the front surface outside the cornea.

3. The irradiating device according to claim 1, wherein said operation beam is constituted by femtosecond laser.

4. has been amended as follows:

A program making a computer comprising:
- an output means which outputs operation beam having a function of making an incision on a cornea of an eye;
- a control means which controls at least an irradiating direction of said operation beam in such a manner as to form an incised site for inserting an intraocular lens into an interior of the eye, the incised site penetrating from an outer front surface of the cornea of the eye to an inner front surface, by the operation beam output from the output means; and
- a setting means which sets a cross sectional shape in a direction intersecting an advancing direction from an opening of the outer front surface of the cornea in said incised site toward an opening of the inner front surface, to the other linear shape than a rectilinear shape in which a convex shape collapsing onto the inner front surface from the outer front surface of the cornea is formed at least in one of both sides of said incised site, in the case of inserting the intraocular lens through said incised site, and accepts an input from a user, wherein said setting means comprises:
- a display means which displays an image of an operation part; and
- a superposition setting means which superposes the image of the operation part displayed by the display means, and accepts an input setting a shape of an advancing route heading for the inner front surface from the outer front surface of the cornea of the eye in the incised site, and a cross sectional shape in a direction intersecting said advancing route in the incised site, and wherein said superposition setting means can accept a cross sectional shape in which said cross sectional shape changes in correspondence to the position on said advancing route in the incised site.

* * * * *